(12) United States Patent
Kidmose et al.

(10) Patent No.: US 9,025,800 B2
(45) Date of Patent: May 5, 2015

(54) HEARING AID ADAPTED FOR DETECTING BRAIN WAVES AND A METHOD FOR ADAPTING SUCH A HEARING AID

(75) Inventors: Preben Kidmose, Maarslet (DK); Danilo P. Mandic, London (GB); Michael Ungstrup, Allerod (DK); David Looney, London (GB); Cheolsoo Park, London (GB); Mike Lind Rank, Farum (DK)

(73) Assignee: Widex A/S, Lynge (DK)

( * ) Notice: Subject to any disclaimer, the term of this patent is extended or adjusted under 35 U.S.C. 154(b) by 0 days.

(21) Appl. No.: 13/348,986

(22) Filed: Jan. 12, 2012

(65) Prior Publication Data
US 2012/0177233 A1    Jul. 12, 2012

Related U.S. Application Data

(63) Continuation-in-part of application No. PCT/EP2010/051005, filed on Jan. 28, 2010.

(30) Foreign Application Priority Data

Jul. 13, 2009  (DK) .................................. 2009 70060

(51) Int. Cl.
*H04R 25/00* (2006.01)
*A61B 5/12* (2006.01)
(Continued)

(52) U.S. Cl.
CPC ............. *A61B 5/121* (2013.01); *A61B 5/04845* (2013.01); *A61B 5/6815* (2013.01); *A61B 5/6838* (2013.01); *G06F 3/015* (2013.01); *H04R 25/70* (2013.01); *H04R 2225/41* (2013.01)

(58) Field of Classification Search
CPC ........ H04R 25/00; H04R 29/00; H04R 25/55; H04R 25/558; H04R 2225/023; H04R 2225/025
USPC .................... 381/60, 312–316, 320–321, 328
See application file for complete search history.

(56) References Cited

U.S. PATENT DOCUMENTS

| | | | |
|---|---|---|---|
| 6,330,339 | B1 | 12/2001 | Ishige et al. |
| 6,493,576 | B1 | 12/2002 | Dankwart-Eder |

(Continued)

FOREIGN PATENT DOCUMENTS

| | | |
|---|---|---|
| DE | 19624133 A1 | 12/1997 |
| JP | 9-182193 A | 7/1997 |

(Continued)

OTHER PUBLICATIONS

Korean Office Action for Korean Application No. 10-2012-7002463 dated Apr. 9, 2013, with English translation.

(Continued)

*Primary Examiner* — Suhan Ni
(74) *Attorney, Agent, or Firm* — Sughrue Mion, PLLC

(57) ABSTRACT

A hearing aid comprises an amplifier (303, 309, 317), an input transducer (301), an output transducer (824) and a signal processing device (825). The amplifier (303, 309, 317) and the signal processing device (825) are connected. The hearing aid further comprises at least two electrodes (201-205) adapted for detecting electrical signals such as brain waves, the at least two electrodes (201-205) being connected to a differential amplifier (303, 309, 317), which in turn is connected to the signal processing device, and means for modifying the operation of said hearing aid in dependence of the detected signals. The invention further provides a method for adaptation of a hearing aid.

20 Claims, 13 Drawing Sheets

(51) Int. Cl.
*A61B 5/0484* (2006.01)
*A61B 5/00* (2006.01)
*G06F 3/01* (2006.01)

(56) References Cited

U.S. PATENT DOCUMENTS

2005/0111680 A1  5/2005  Meier et al.
2006/0093997 A1  5/2006  Kearby et al.

FOREIGN PATENT DOCUMENTS

| JP | 9-327097 A | 12/1997 |
| JP | 9-327445 A | 12/1997 |
| JP | 2000-262481 A | 9/2000 |
| JP | 2008-086392 A | 4/2008 |
| JP | 2008-295867 A | 12/2008 |
| WO | 2006047874 A1 | 5/2006 |
| WO | 2007047667 A2 | 4/2007 |
| WO | 2008116462 A1 | 10/2008 |
| WO | 2009045449 A1 | 4/2009 |

OTHER PUBLICATIONS

Japanese Office Action for Japanese Patent Application No. 2012-519938 dated Feb. 19, 2013 with English Abstract.
Office Action for Japanese Patent Application No. 2012519938 dated Sep. 10, 2013, with English translation.
International Search Report for PCT/EP2010/051005 dated Mar. 29, 2010.
Office Action for counterpart Chinese Application No. 201080031697.9 dated Jan. 3, 2014.

HEARING AID ADAPTED FOR DETECTING BRAIN WAVES AND A METHOD FOR ADAPTING SUCH A HEARING AID

RELATED APPLICATIONS

The present application is a continuation-in-part of application PCT/EP2010/051005, filed on Jan. 28, 2010, in Europe and published as WO2011006681 A1.

The present invention is based on and claims priority from PA200970060, filed on Jul. 13, 2009, in Denmark, the contents of which are incorporated here by reference.

BACKGROUND OF THE INVENTION

1. Field of the Invention

The present invention relates to hearing aids. The invention generally relates to hearing aids capable of measuring brain waves and adjusting the signal processing according to the measured signals, and more specifically to such hearing aids comprising an amplifier, an input transducer, an output transducer and a signal processing device, and where said amplifier and said signal processing device are connected. The invention further relates to a method for adaptation of a hearing aid.

2. The Prior Art

It is generally known, particularly within medical science, to measure brain waves by placing electrodes on the scalp of a subject, whose brain waves it is desired to measure (for simplicity denoted "subject" in the following), and to view, process and interpret the measured brain waves using suitable equipment. Typically, such equipment is an electroencephalograph, by means of which a so-called electroencephalogram (EEG) may be achieved. Such an EEG results from a measurement and recording of electrical activity in a subject's brain by measuring the electric potential generated on the surface of the subject's scalp by currents flowing between synapses in the subject's brain. Within medical science EEG's are used for various diagnostic purposes.

A system for such a use is known from WO-A1-2006/047874, which describes measurement of brain waves by use of electrodes placed in connection with at least one of the ears of the subject, i.e. placed on an outer ear part or placed in the ear canal. The measurements are used particularly for detecting the onset of an epileptic seizure. WO-A1-2006/047874 also describes the use of electrodes in pairs as detection and reference electrodes respectively, such a setup being well known in the field of electroencephalography.

Furthermore it is known from WO-A1-2008/116462 to measure the hearing ability of the subject by using a hearing aid to generate a test stimulus signal and transmit said signal to a subject as an acoustic stimulus, and by detecting a brain wave response to said acoustic stimulus signal by use of separate electrodes placed on the subject's scalp and to transmit the brain wave response to an electrophysiological instrument such as an electroencephalograph for processing.

However, at least the signal processing devices of the known systems are, due to their complexity and use of extensive and complicated equipment, confined to use and operation by qualified staff. Furthermore the placement of in by far most cases electrodes and in any case associated wiring on various parts of the subject's scalp and head renders the known systems rather unattractive for use outside laboratory surroundings, thus rendering exploitation of the advantages related to the use of brain wave measurements outside the laboratory rather cumbersome.

SUMMARY OF THE INVENTION

The present invention therefore aims at providing a hearing aid in which brain wave measurements such as EEGs become possible without or with a minimum of use of extensive and complicated equipment, which hearing aid may be used in an uncomplicated way in everyday life, and with which the advantages related to the use of brain wave measurements in hearing aids may be readily utilized outside the laboratory.

The invention, in a first aspect, provides a hearing aid comprising an amplifier, an input transducer, an output transducer and a signal processing device, the amplifier and the signal processing device being connected; at least two electrodes adapted for detecting electrical signals such as brain waves, the at least two electrodes being connected to a differential amplifier, which in turn is connected to the signal processing device; and means for modifying the operation of said hearing aid in response to the detected signals.

Thereby a hearing aid is provided with which a subject's brain waves may be monitored and measured, and with which the thus measured brain waves may be processed internally in the hearing aid. With such a hearing aid, it is no longer necessary to use external equipment for measuring brain waves and processing the measured signals, and it is inconspicuous when worn by the user and thus more attractive to wear outside the laboratory.

Enabling the measurement of brain waves during everyday life by using a hearing aid according to the invention has a variety of uses and advantages.

Most notable it has been shown by the inventors that it is, somewhat surprisingly, possible to use brain wave measurements to estimate to which part of an acoustic image the user pays attention. The details of such an estimation will be described further below.

When it can be measured to which part of an acoustic image the user pays attention, this information may be used as valuable feedback for the hearing aid algorithms in order to enable adaptation of the hearing aid to obtain optimum intelligibility of the particular part of an acoustic image, to which the user pays attention, without the user needing to consciously act to adapt the hearing aid. Such control of a hearing aid is particularly useful in situations where a user is focused on a particular part of a complex acoustic image. This may for instance be the case when a hearing aid user is trying to discern a certain source of sound, such as the speech of a particular person, a speaker announcement or music playing, in an acoustic image comprising multiple sound sources.

This forms a contrast to the present methods for emphasizing or suppressing a part of an acoustic image. Presently the user may manually change the program of the hearing aid to, say, a music program, and the presence of noise may be detected by the use of the microphone of the hearing aid. Noise may then be suppressed by running suitable algorithms in the signal processing device of the hearing aid.

Other advantageous uses and advantages related to measurement of brain waves using hearing aids include, but are not limited to, the following:

a) Monitoring the development in a user's hearing loss with the natural sound environment as stimulus using Auditory Brainstem Response (ABR)-like or Auditory Steady State Response (ASSR)-like measurements, thereby enabling "on-the-fly" fitting, i.e. fitting when needed, of the hearing aid.

b) Measurement of the user's hearing threshold, e.g. by the use of Auditory Brainstem Response (ABR) measurements to obtain an objective image of the hearing threshold without needing any interaction from the user, which is particularly desirable in connection with small children and persons with strongly impaired cognitive abilities.

c) Use as a type of brain-computer interface, e.g. controlling the hearing aid by use of EEG-recognition. In a brain-computer interface the user will be able to control the hearing aid by consciously focusing thought on the desired action, e.g. changing the program of the hearing aid, the desired action being linked to a detectable "thought", e.g. such as to imagine moving the right arm without actually doing so. In a brain-computer interface the EEG-signal will be used to detect such an event and will thus be able to partly or fully take the place of a remote control.

According to a preferred embodiment, said signal processing device comprises feature extraction means for extracting at least one feature from a signal detected by means of said at least two electrodes, and classifying means for classifying said at least one feature extracted by said feature extraction means. Thereby the possibility of focusing on one particular feature carried by the measured brain wave signal and comprising desired perceptive information regarding the subject is provided. The particular feature to be extracted by the feature extraction means depends on the particular functionality that is to be incorporated in the hearing aid.

This embodiment is particularly useful when it is desired to use the hearing aid to perform brain wave signal measurements in order to estimate to which part of an acoustic image the user pays attention, as described above.

According to a preferred embodiment, the hearing aid further comprises a microphone connected to the feature extraction means, whereby the acoustic image detected by the microphone may serve as additional information in the processing of the signals detected by the electrodes.

According to a preferred embodiment, the hearing aid further comprises means for comparing a signal detected by means of said at least two electrodes with a predefined set of attention classes, thus providing for automatic detection of the part of an acoustic image focussed upon by the user of the hearing aid.

By the term "attention class(es)" as used herein is, without being limited thereto, meant one or more of the main attention classes "signal type", i.e. the type of signal in an acoustic image, the user's "spatial focus" and the user's "mental focus". The main attention class "signal type" may comprise such sub-classes as speech, music, noise and the like. The main attention class "spatial focus" may comprise such sub-classes as broad/narrow, left/right and the like. The main attention class "mental focus" may comprise such sub-classes as interest in surroundings, concentrated, relaxed and the like.

According to a particularly preferred embodiment, the means for modifying the operation of the hearing aid modifies the operation of the hearing aid in response to said at least one feature extracted by said feature extraction means, thus providing for automatic adaptation of the hearing aid to the given part of an acoustic image focussed upon by the user of the hearing aid.

According to a preferred embodiment, the means for modifying the operation of the hearing aid is activated by the hearing aid upon recognizing, particularly by means of said signal processing device, a detected signal as comprising characteristics of at least one of a hearing threshold measurement, a hearing loss measurement, an attention focus measurement and a Brain-Computer Interface (BCI) action measurement. Thereby adjustment of the hearing aid will be performed relating to hearing threshold, hearing loss, attention focus and/or a BCI action, thus simplifying the adjustment process and avoiding adjustment due to unrelated features of the detected signal.

According to a particularly preferred embodiment, the at least two electrodes are arranged on or in a surface of a part of the hearing aid, preferably a plug of said hearing aid, such that when said hearing aid is worn by a user, said at least two electrodes are in physical contact with tissue of said user, thereby providing for enhanced quality and signal strength in the detection of the brain wave signals.

According to a further embodiment, the hearing aid further comprises a fluid, conductive gel in connection with said at least two electrodes, whereby improved signal detection quality is provided. However, other generally known electrode materials suitable for this purpose may also be employed.

According to a particularly preferred embodiment, said at least two electrodes are silver electrodes, such electrodes providing for a particularly good durability when exposed to the environmental conditions in the ear canal of a user.

The invention, in a second aspect, provides a hearing aid system comprising a first and a second hearing aid, each one of the first and the second hearing aid having an amplifier, an input transducer, an output transducer and a signal processing device, said amplifier and said signal processing device being connected; at least two electrodes adapted for detecting electrical signals such as brain waves, the at least two electrodes being connected to a differential amplifier, which in turn is connected to the signal processing device; and means for modifying the operation of said hearing aid in response to the detected signals, and at least one of the first and second hearing aid comprising a signal processing device comprising a feature extraction means and a classifying means, and wherein at least one of the first and second hearing aids comprises transmitting means for transmitting information to the second or first hearing aid, respectively.

With such a system it becomes possible to compare signals measured by each of the two hearing aids, for instance in each ear of a user. Thereby the sound perception and thereby e.g. the hearing ability of each ear may be measured, compared and monitored.

As the left brain hemisphere is known to perform logical thinking processes, and the right brain hemisphere more abstract thinking processes, it is further feasible that the right and left hearing aids, respectively, may detect different signals resulting from different thinking processes that may then be compared.

According to further preferred embodiments of the hearing aid system, the signal processing means further comprises a class combining means, the feature extraction means and/or classification means and/or class combining means of said first and second hearing aid, respectively, are interconnected by means of said transmitting means, and said transmitting means is wireless. This provides the possibility of transmitting, by wired or wireless connection, and thereby of monitoring and comparing, particular features and measurements between the hearing aids of the hearing aid system. The usage of wireless transmitting means makes the hearing aid system particularly convenient to use.

The invention, in a third aspect, provides a method for adaptation of a hearing aid during use by a user, the method comprising the following steps: providing a hearing aid, said hearing aid having an amplifier, an input transducer, an output transducer and a signal processing device, said amplifier and said signal processing device being connected; at least two electrodes adapted for detecting electrical signals such as brain waves, the at least two electrodes being connected to a differential amplifier, which in turn is connected to the signal processing device; and means for modifying the operation of said hearing aid in response to the detected signals, measuring a brain signal from said user, and adjusting the operation of said hearing aid in response to the detected signal.

According to a particularly preferred embodiment, the method comprises the further step of comparing said measured signal with a predefined set of attention classes.

According to a particularly preferred embodiment, said measuring, comparing and adjusting steps are repeated with a predetermined frequency.

According to another particularly preferred embodiment, said comparing step comprises extracting a feature from the measured brain signal by executing a first algorithm in said signal processing device, and classifying said feature by executing a second algorithm in said signal processing device.

BRIEF DESCRIPTION OF THE DRAWINGS

The invention will now be described in further detail based on a non-limiting exemplary embodiment, and with reference to the drawings. In the drawings.

DETAILED DESCRIPTION OF THE INVENTION

Figure 1:
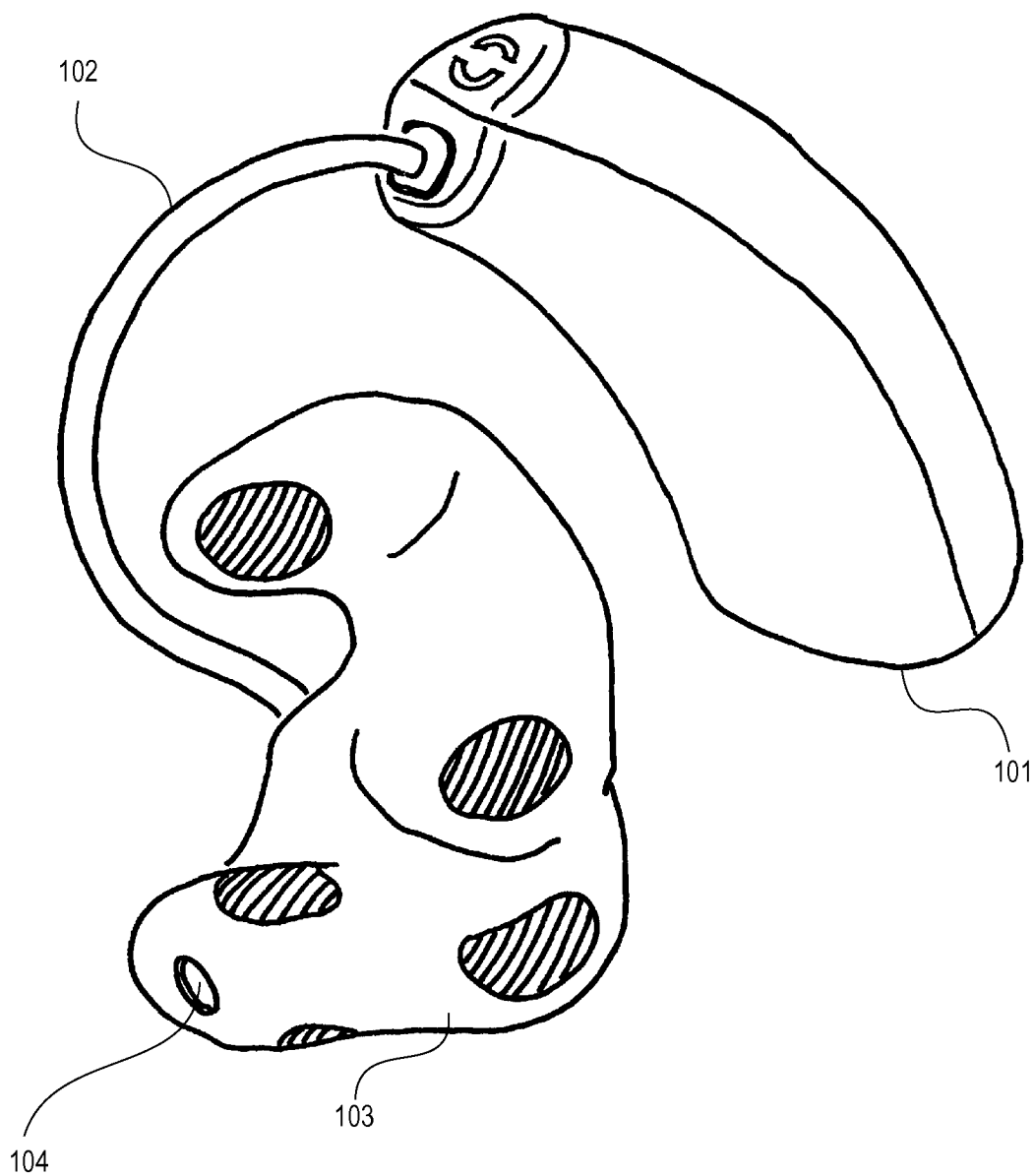
FIG. 1 illustrates an embodiment of a hearing aid according to the invention.

FIG. 1 shows a preferred embodiment of a hearing aid according to the invention comprising a behind-the-ear (BTE) component 101, a plug 103 for insertion in the ear canal of a user, i.e. an in-the-ear (ITE) component, and a connection means 102 for connecting the BTEcomponent 101 and the plug 103. The plug 103 comprises a surface and a connection opening 104.

The connection opening 104 is the opening through which sound is transmitted from the HA to the ear canal and thereby the ear drum of the user. In the case of an ordinary BTE hearing aid the connection opening 104 is for direct connection with the connection means 102. In case of a receiver-in-the-ear (RITE) hearing aid the connection opening 104 is for connecting the connection means 102 and the receiver.

A hearing aid plug, such as the plug 103, is preferably custom moulded to fit the ear, preferably the ear canal, of a user. When inserted in the ear, preferably in the ear canal, of the user the surface of the plug 103 will lie adjacent to and in physical contact with the tissue of the ear of the user. It is noted that the hearing aid according to the invention may in principle be any type of hearing aid.

Figure 2:
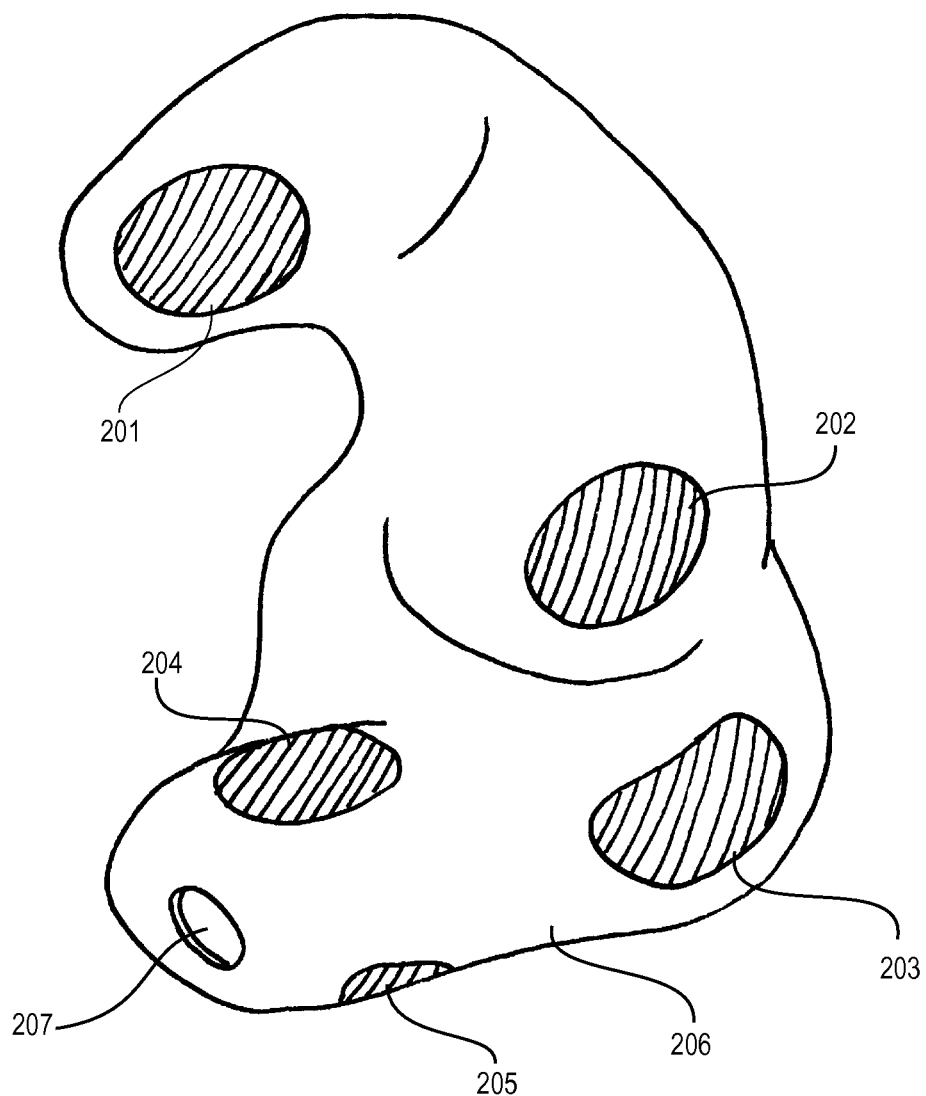
FIG. 2 illustrates a plug for a hearing aid according to FIG. 1.

Referring to FIG. 2, the hearing aid further comprises five electrodes 201, 202, 203, 204 and 205 adapted for detecting electrical signals such as brain waves. The actual detection that will be described in detail below is preferably performed with respect to a reference point. The electrodes 201-205 are arranged on the surface of the plug 206 (103 in FIG. 1) of the hearing aid. Alternatively the electrodes 201-205 may be embedded in the surface of the plug 206, or be arranged on or imbedded in the surface of another part of the hearing aid. The exact number of electrodes 201-205 provided may be more or less than the five electrodes 201-205 shown and remain uncritical. However, the provision of at least two electrodes is preferred, as such a configuration provide for the possibility of allowing at least one of the electrodes to act as reference point, thus being a reference electrode, for the remaining electrodes, thus being detecting electrodes, thereby improving the quality of the measured signals. Alternatively the electrodes 201-205 may be set up to operate in clusters, e.g. in pairs, with one electrode acting as a reference electrode for one or more other electrodes, thus acting as detecting electrode(s). Preferably the electrodes 201-205 are made of silver, as silver is known to have properties providing for good resistance to the harsh environment present in the human ear canal. However, any material suitable for resisting the environment in the ear canal of a human may in principle be used.

In order to further improve the quality of the signals detected by means of the electrodes 201-205, the hearing aid may comprise a conductive gel (not shown) in connection with the electrodes 201-205.

Figure 3:
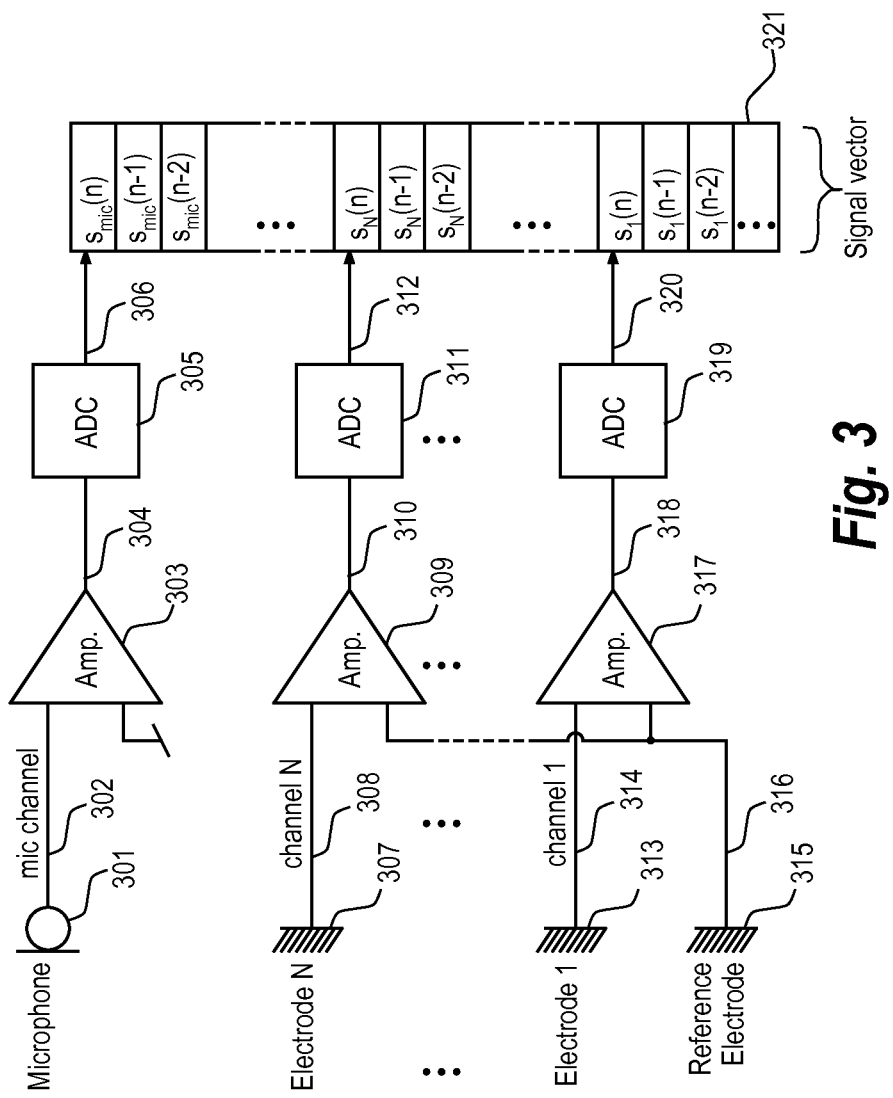
FIG. 3 is a flow diagram illustrating an embodiment of a signal detection path through a differential amplifier, i.e. the initial part of the signal processing path known as the "analog front-end", of a hearing aid according to an embodiment of the invention.

Turning to FIG. 3 a flow diagram illustrating an embodiment of the initial part of the electronics of the hearing aid according to the invention is shown. This initial part of the electronics is known as the analog front-end. The analog front-end as shown is connected to a plurality of electrodes (electrodes 1 to N), of which FIG. 3 for the sake of simplicity shows only the first electrode 313 and the Nth electrode 307, from which input signals are received. The electrodes 307 and 313 are by means of channels 308 and 314 each connected to a differential amplifier 309 and 317, respectively, for receiving and amplifying the signal detected by the electrodes 307 and 313. Each of the differential amplifiers 309 and 317 also receives input from a reference electrode 315 by means of a channel 316. The differential amplifiers 309 and 317 are connected to a respective analog digital converter (ADC) 311 and 319.

Furthermore, the initial part of the electronics comprises an input transducer, in FIG. 3 shown as a microphone 301. The microphone 301 is connected to the analog front-end through a microphone channel 302 connected to an amplifier 303, which is connected to an ADC 305. Thereby the acoustic image detected by the microphone 301 may serve as additional information in the processing of the signals detected by the electrodes 307, 313 and 315.

The ADC's 305, 311, 319 sample the respective amplified signals 304, 310, 318 received from the amplifier 303 and the differential amplifiers 309, 317, thereby creating output signals 306, 312, 320 being discrete in time. It is noted that the sampling frequencies for the microphone signal 306 may differ from those of the electrode signals 312, 320. The output signals 306, 312, 320 from each ADC 305, 311, 319 constitute in combination a signal vector 321, that may be written as s=s(i,n), i denoting the origin of signal being sampled, i.e. electrode number i, and n denoting the sampling time. Thereby the signal vector 321 may be regarded as a signal in time and space, or as a time dependent vector. The signal vector 321 serves as input for the subsequent signal processing in the hearing aid, as will be explained below.

Figure 4:
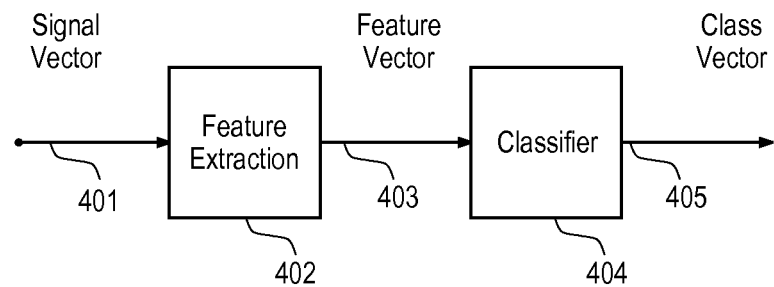
FIG. 4 is a flow diagram illustrating the principle of the feature extraction and classification process in a hearing aid according to an embodiment of the invention.

Turning to FIG. 4 the principle of the feature extraction and feature classification process in a hearing aid according to the invention is illustrated. The signal vector 401 (321 in FIG. 3) is used as input for a feature extraction means 402. The output from the feature extraction means 402 is one or more extracted features, herein termed as "feature vector" 403, which serve as input for a classifying means 404 classifying the extracted features of the feature vector 403. The output of the classifying means 404 is at least one indicator of an attention class, the term attention class as used herein being defined in the initial part of the description. The indicator may either indicate one of a number of attention classes (hard classifier) or be a probability vector giving probabilities for each attention class (soft classifier). In the following the output of the classifying means 404 will be termed "class vector" 405. The class vector 405 is transmitted as an output to be used in further signal processing means of the hearing aid.

To further clarify the functionality of the feature extraction means 402 and the classifying means 404, one may consider the feature extraction, f, and the classification, c, as dimension reducing mappings of the space S of signal vectors 401, the signal vector 401 being of high dimension:

$f: S \rightarrow F$ and $c: F \rightarrow C$ where F is the space of feature vectors 403 of a lower dimension and C is the set of attention classes of yet lower dimension constituting the class vector 405. It is likely to be expected that both the feature extraction, f, and the classification, c, will have to be trained to adapt to the individual user.

Figure 5:
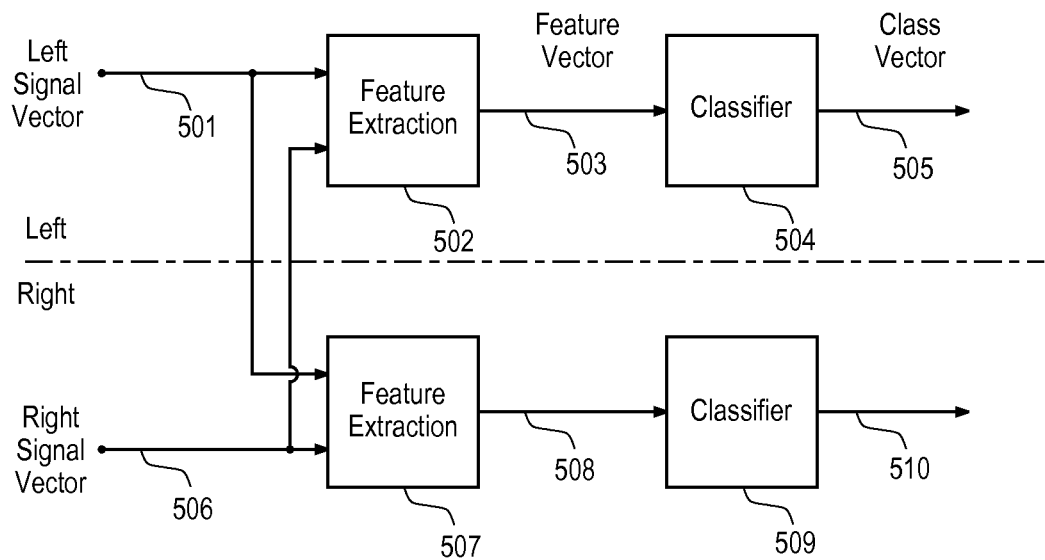
FIG. 5 is a flow diagram illustrating a first embodiment of the principle of the feature extraction and classification process in a hearing aid system according to the invention.

In FIG. 5 a first embodiment of the principle of the feature extraction and feature classification process in a hearing aid system according to the invention is illustrated. The hearing aid system comprises a first, e.g. left, hearing aid illustrated above the dashed line in FIG. 5 and a second, e.g. right, hearing aid illustrated below the dashed line in FIG. 5. The first and second hearing aids are both hearing aids according to the invention and substantially as described above with reference to FIGS. 1 and 2. In the embodiment shown, in each of the left and right hearing aids, an analog front-end substantially as described above generates a left signal vector 501 and a right signal vector 506, respectively. In each of the left and right hearing aids the respective signal vector 501 and 506 is used as input for a feature extraction and classification process of the type described in connection with FIG. 4. Thus, the respective signal vectors 501 and 506 are used as input for a feature extraction means 502 and 507, respectively, creating feature vectors 503 and 508, respectively, which are in turn used as input for a classification means 504 and 509, respectively, creating a class vector 505 and 510, respectively.

Furthermore, the feature extraction means 502 and 507 are by means of a transmitting means (shown as arrows on FIG. 5) interconnected for exchange of signal vectors 501 and 506. The transmitting means is a wireless transmitting means, preferably adapted for two-way communication between the hearing aids, but may in principle be any suitable transmitting means. Such a hearing aid system allows for instance for collecting a larger quantity of signals, thus providing a larger quantity of information to the signal processing device performing the final signal processing.

Figure 6:
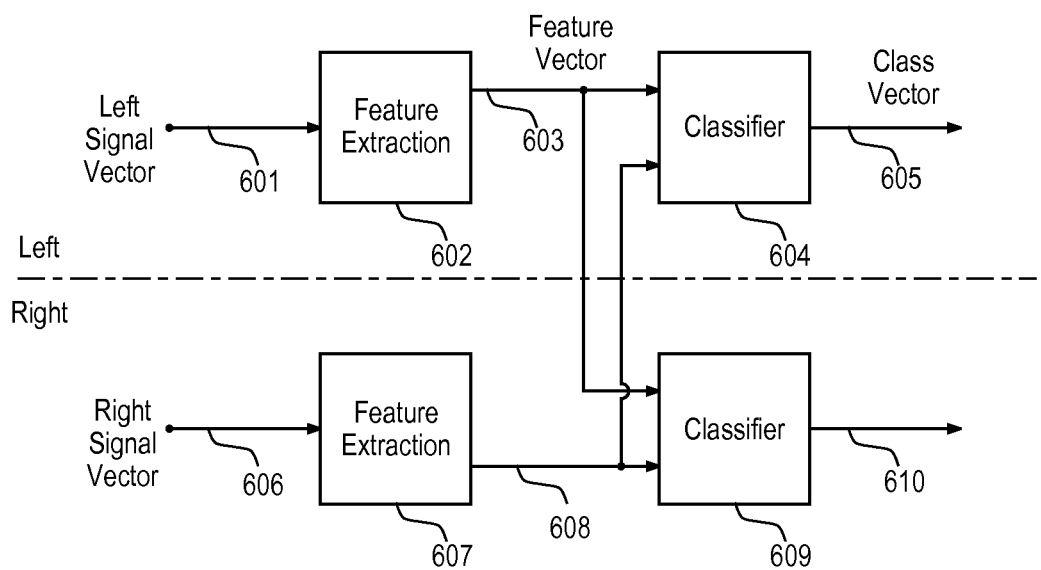
FIG. 6 is a flow diagram illustrating a seceond embodiment of the principle of the feature extraction and classification process in a hearing aid system according to the invention

The transmitting means may in principle form a connection between the hearing aids connecting other components than the above mentioned. For instance, and as illustrated in FIG. 6, featuring a second embodiment of the process shown of FIG. 5, the interconnection may be provided between the classifying means 604 and 609, respectively, of the hearing aids, thus enabling exchange of feature vectors 603 and 608, respectively, between the hearing aids.

Figure 7:
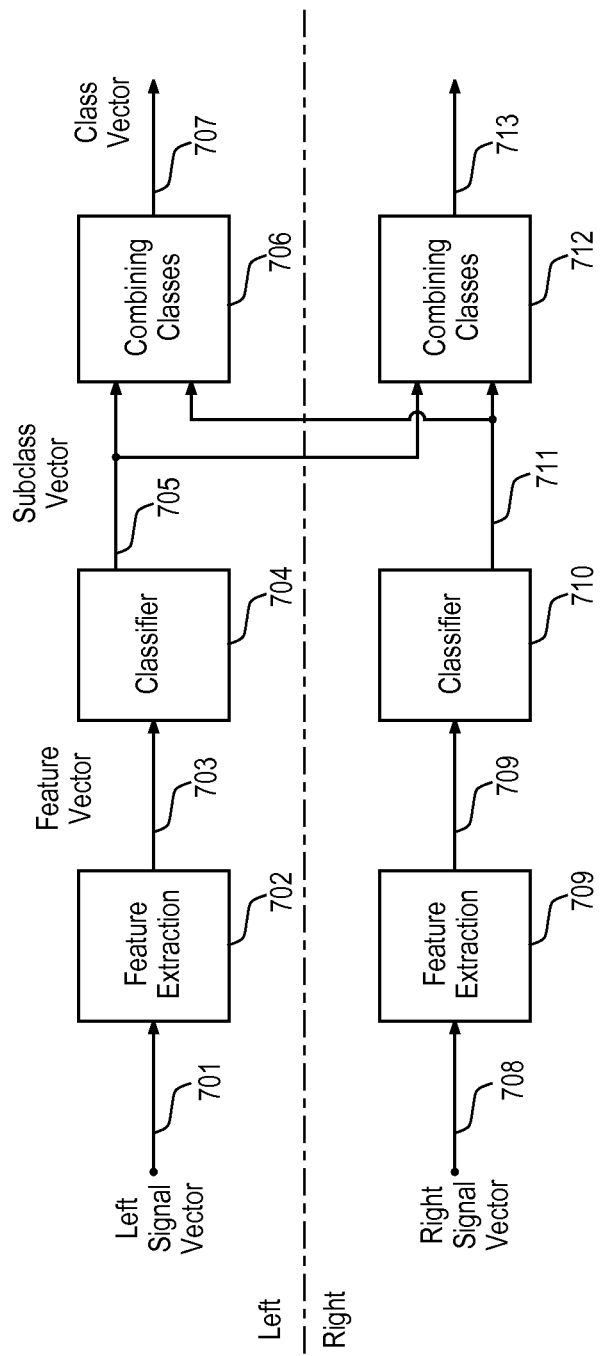
FIG. 7 is a flow diagram illustrating a third embodiment of the principle of the feature extraction and classification process in a hearing aid system according to the invention

As illustrated in FIG. 7, featuring a third embodiment of the process shown of FIG. 5, another possibility is to provide an interconnection for exchanging the output of the respective classification means 704 and 710, in FIG. 7 called subclass vectors 705 and 711. In this case, each hearing aid of the hearing aid system further comprises class combining means 706 and 712, respectively, for combining the subclass vectors 705 and 711, respectively, to form the final class vector 707 and 713, respectively.

Figure 8:
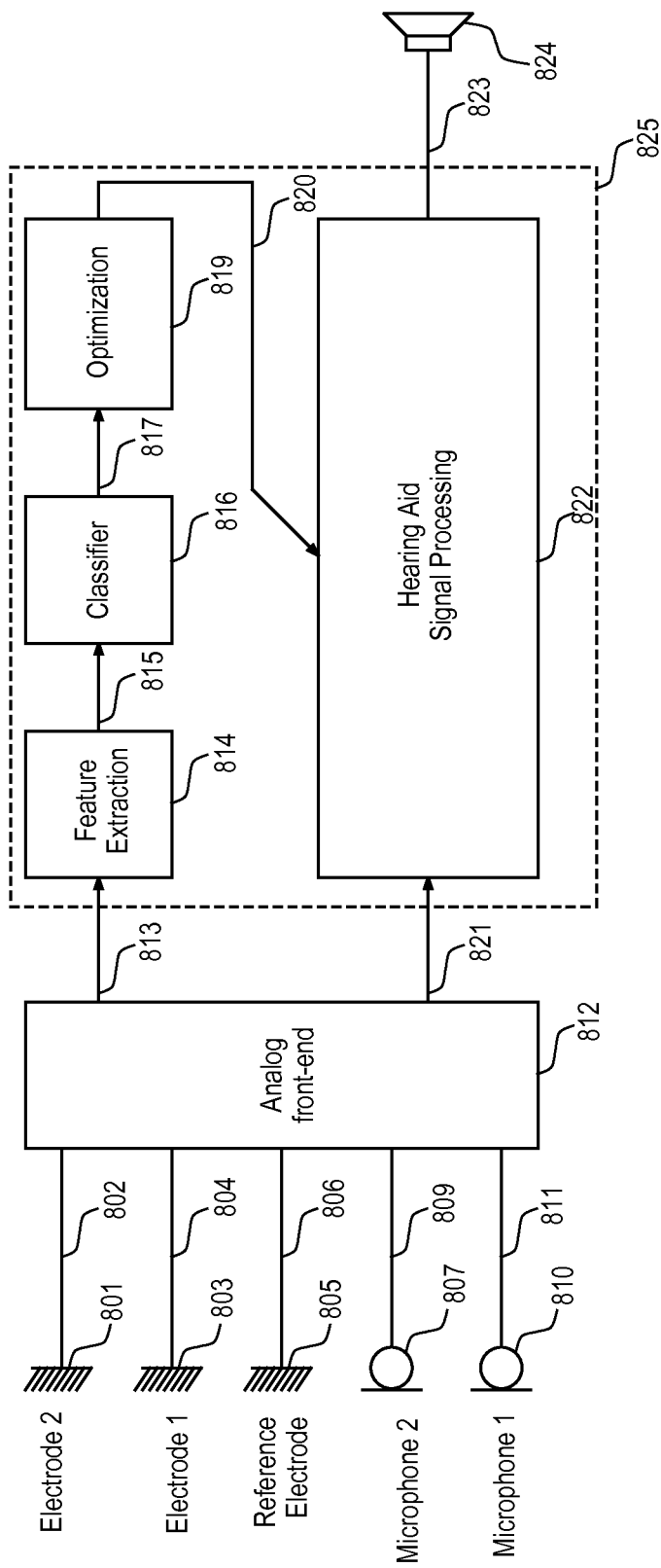
FIG. 8 is a flow diagram illustrating an embodiment of the complete signal detection and processing path of a hearing aid according to the invention.

Turning to FIG. 8 a flow diagram illustrating the complete signal obtaining and processing path in a hearing aid according to the invention is shown. The hearing aid comprises electrodes 801, 803, a reference electrode 805 and input transducers in the form of microphones 807 and 810 connected to and transmitting signals 802, 804, 806, 809 and 811, respectively, to the analog front-end 812. The output of the analog front-end 812, i.e. the signal vector 813, 821, is fed to the digital back-end 825. The output of the digital back-end 825 is a signal being fed to an output transducer of the hearing aid, in the case shown as a speaker signal 823 being fed to a speaker 824. The speaker signal 823 fed to the speaker 824 is generally an analog signal achieved by means of a digital-analog converter (not shown) e.g. placed in or on the digital back-end 824.

The digital back-end 825 comprises a circuit for feature extraction and classification according to the method described in connection with FIG. 4, thus comprising feature extraction 814 performed on the signal vector 813 and classification 816 performed on the feature vector 815. In the digital back-end 825, the class vector 817 obtained by classification 816 is used as input for a means—in FIG. 8 denoted optimization 819—for comparing the attention classes of the class vector 817 with a predefined set of attention classes. The optimization 819 is intended to optimize the hearing aid algorithms based on the part of a sound image the user is concentrating focus on. For instance the noise reduction of the hearing aid should work differently depending on whether speech or music is listened to. One way of visualizing this is to picture a cost function in which the weighting of the individual terms of the cost function depend on the attention class. The cost function is furthermore a function of the hearing aid parameters that are to be optimized. The optimization 819 would thus comprise the cost function and a numeric algorithm adapted to find optimum for the cost function. Input for the optimization 819 is the attention class and output is parameters affecting the processing of sound in the hearing aid itself. The output 820 from the optimization 819 is fed to a hearing aid signal processing unit 822 comprising means for modifying the operation of the hearing aid in response to the output 820, and thus essentially to the features initially extracted by the feature extraction means 814.

Furthermore the signal processing unit 822 may comprise means (not shown) for, e.g. acoustically, letting the user know e.g. if the hearing aid has been incorrectly positioned in the ear canal or is malfunctioning.

Furthermore the unit 822 may comprise means (not shown) for processing the signal 821 obtained by the microphones and fed directly from analog front-end 812 to the unit 822. Such a means may e.g. comprise a directional system, a compressor, noise reduction means and feedback cancelling means.

Figure 9A:
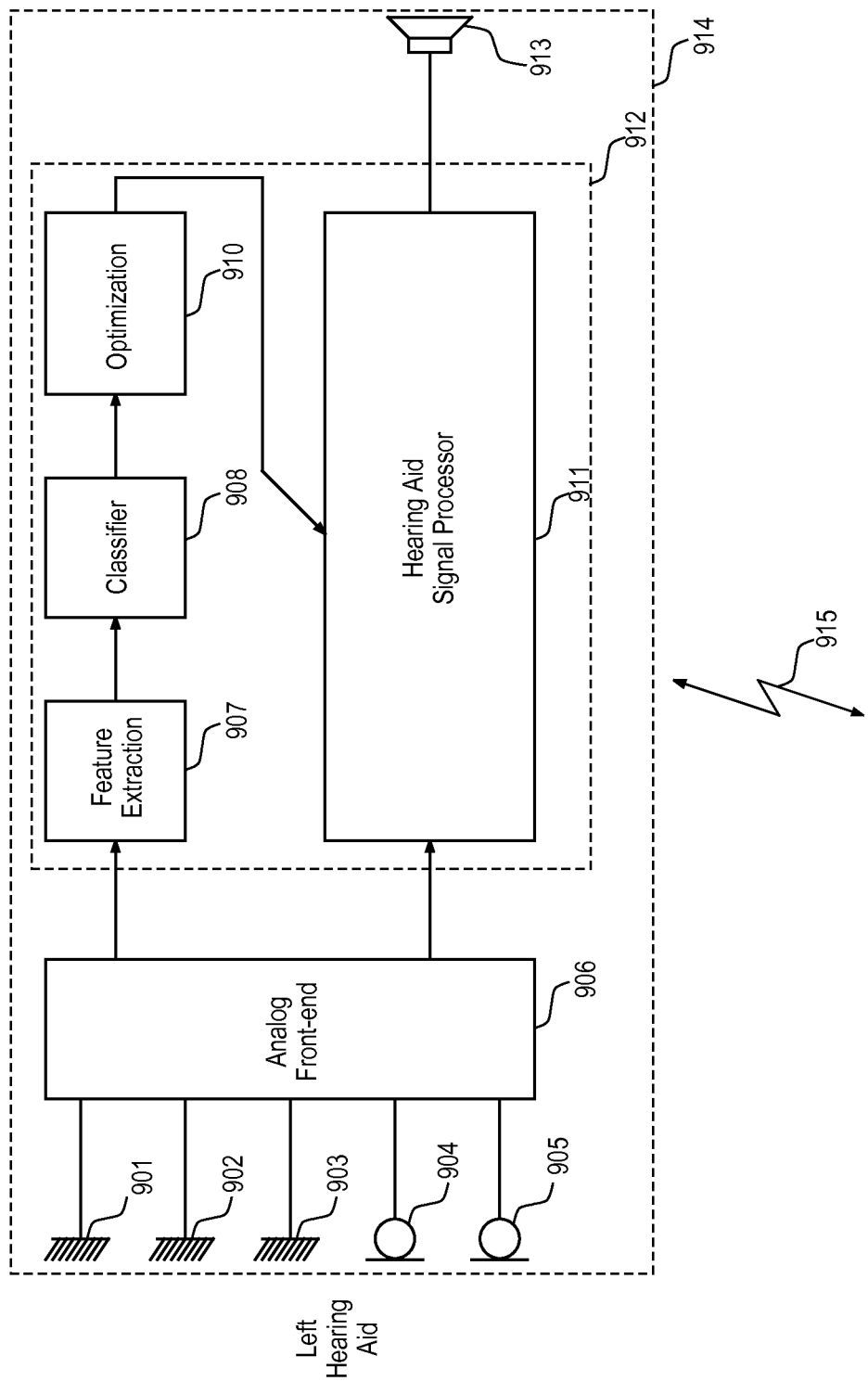
FIGS. 9a and 9b show in combination a flow diagram illustrating an embodiment of the complete signal detection and processing path of a hearing aid system according to the invention.
Figure 9B:
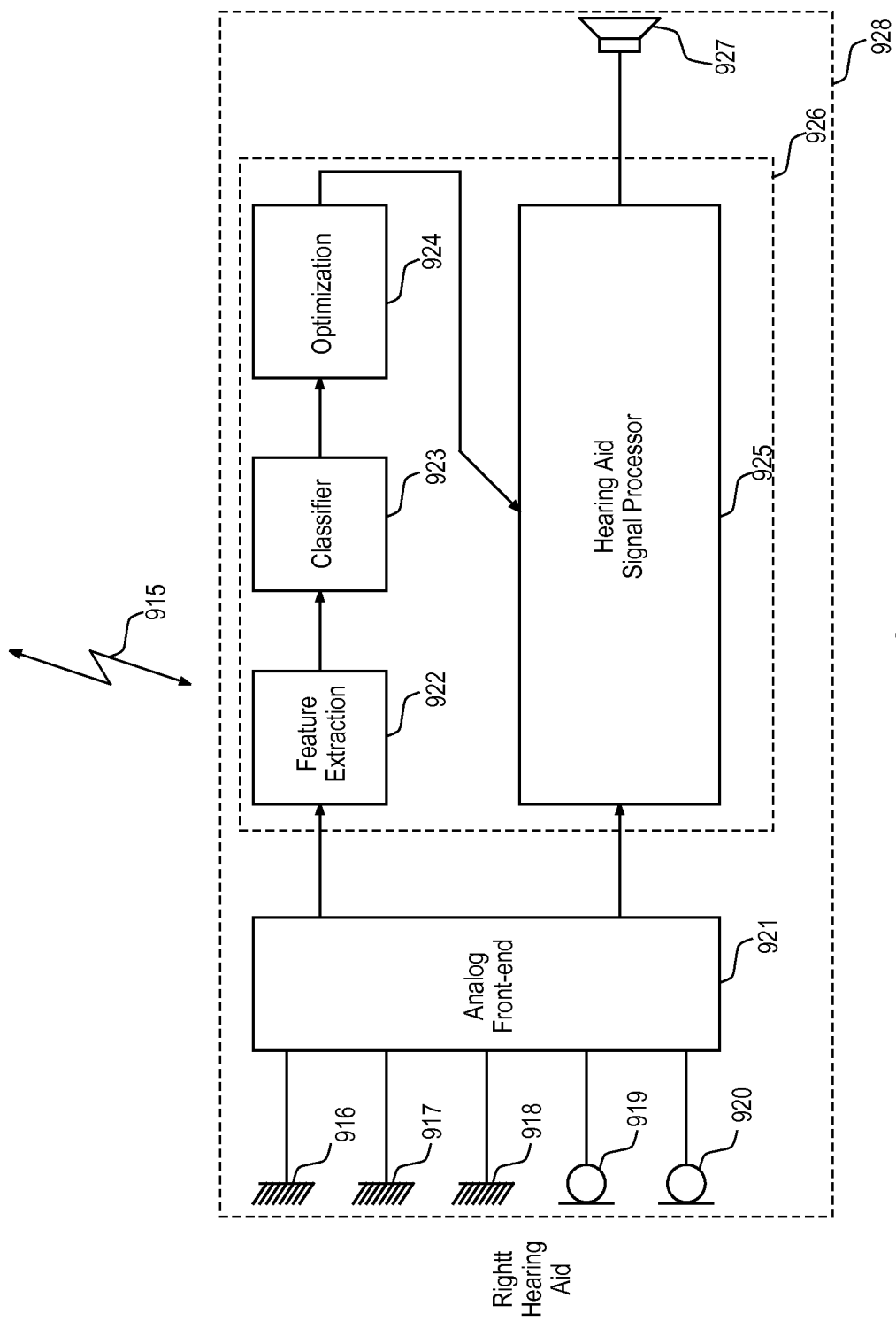

FIGS. 9a and 9b show in combination a flow diagram illustrating the complete signal obtaining and processing in a hearing aid system according to the invention comprising a left 914 (FIG. 9a) and a right 928 (FIG. 9b) hearing aid. The left 914 and right 928 hearing aids are both substantially hearing aids of the type described in connection with FIG. 8. The hearing aid system, however, further comprises a transmitting means 915, preferably a wireless transmitting means, for exchanging information between the hearing aids 914 and 928. The functionality of the hearing aid system differs from that of the hearing aid according to FIG. 8 only in that in that feature extraction 907 and 922 as well as classification 908 and 923 are performed according to one of the methods described in connection with FIGS. 5, 6 and 7.

Thus the transmitting means 915 generally forms a connection between two optional components of the respective hearing aids 914 and 928 of the hearing aid system, but preferably a connection according to either one of FIGS. 5, 6 and 7. Furthermore the transmitting means 915 may be adapted to enable the connection formed between the hearing aids 914 and 928 to be altered according to desire or need.

In the following, examples of the signal processing to be performed in a signal processing device of a hearing aid according to the invention based on recorded EEG-data will be described in further details. The examples will concern the somewhat surprising possibility of using the hearing aid to detect brain waves in order to estimate to which part of an acoustic image the user pays attention, i.e. attention focus.

Experimental Setup

An experiment was set up using a stereo signal with two sound sources. The sound sources are continuous speech and music, respectively. The location of the sound sources remains fixed over all trials with speech coming from the right channel and music from the left channel of the stereo signal. For each trial in the experiment the test subject is required to listen to the stereo signal for approximately 30 seconds and is given instructions to concentrate focus on either speech or music for the entire length of a trial and to alternate focus between trials.

By playing the same stereo signal in all trials it is ensured that factors, which are not directly or indirectly linked to attention, are eliminated. This is based on the assumption that the difference between focus on speech and music, respectively, that may be measured originates from feedback from cognitive layers in the brain to "lower" perceptual or sensory layers.

The experiment is designed to balance out brain responses that are not directly or indirectly related to the attention and also to balance out external factors and sources.

Experiments were conducted in a sound booth. Data in the form of EEG-data were recorded from four subjects using a gMOBIlab+portable biosignal acquisition system (8 electrodes, unipolar recording). The subjects were asked to listen to the same audio track with spatially separated music/speech recording and to shift their attention from music to speech or from speech to music between trials.

Each EEG recording contains 8 channels, and the sampling frequency was 256 Hz, which in the experiments conducted is sufficient for capturing the brain electricity activity. The experiment was performed over 24 trials, i.e. 12 with attention focus on speech, 12 with attention focus on music.

Experimental Results a) Spectrum Analysis

Figure 10A:
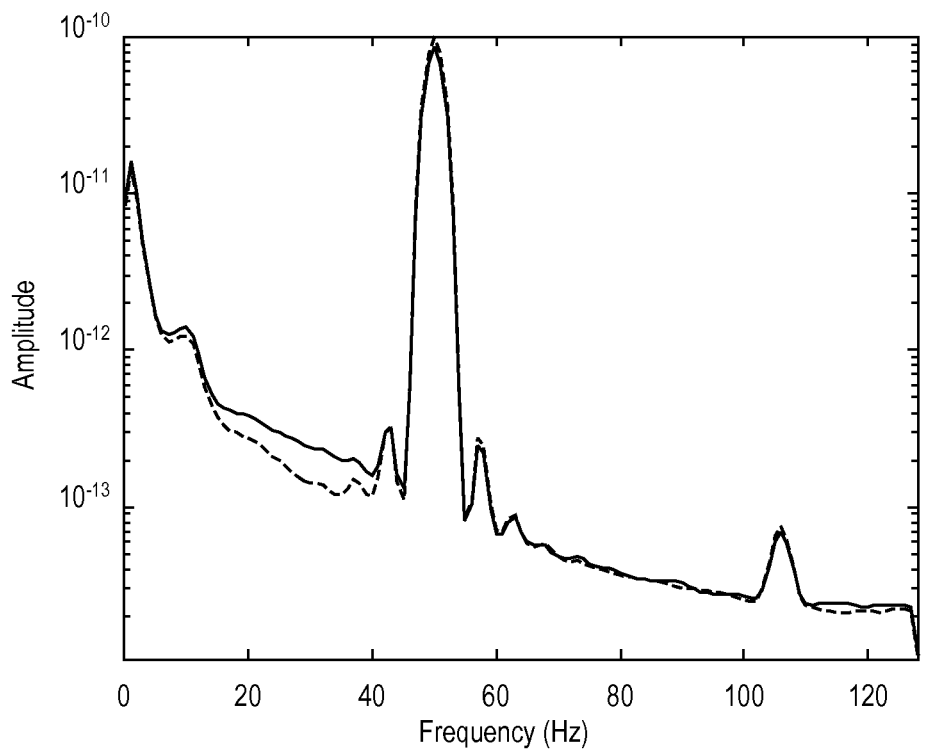
FIG. 10a illustrates the result of a spectrum analysis on the results of a 24 trial measurement of brainwaves from a subject paying attention to speech (dashed line) and music (solid line) respectively.
Figure 10B:
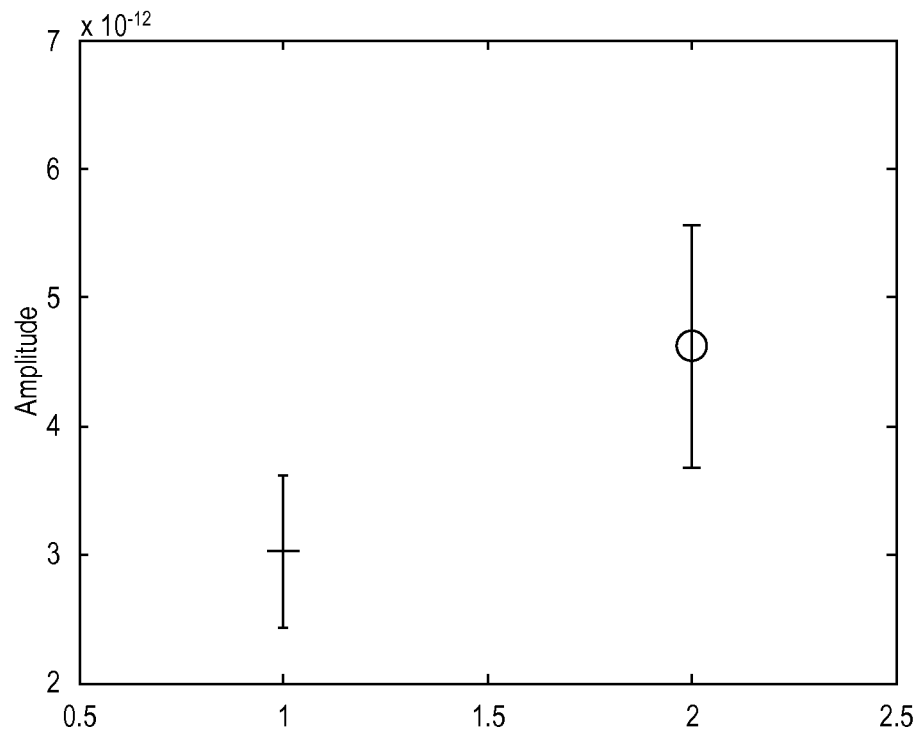
FIG. 10b illustrates the mean value and standard deviation for the interval 20 to 35 Hz of the power spectra of FIG. 10a, FIG. 11 illustrates the result of an auto-regressive analysis (AR-analysis) on the results of a 24 trial measurement of brainwaves from a subject paying attention to speech (marked with "+") and music (marked with "o") respectively.

FIGS. 10a and 10b show the result of a spectrum analysis performed on a 29 second time segment for each trial. A periodogram was applied to perform Power Spectrum Density (PSD) analysis using a series of overlapping windows of length N, N being set to 100. The spectrum analysis describes the total amount of energy of the signal in a given frequency band.

The mean power spectrum shown in FIG. 10a, featuring speech with dashed line and music with solid line, was determined from the windowed data.

FIG. 10b shows the mean value and the standard deviation for the total energy in the frequency interval 20 to 35 Hz of the spectrum shown in FIG. 10a. Trials with attention to speech are denoted with "+", trials with attention to music with "o". The significant difference in amplitude illustrated in FIG. 10b reveals that it is possible to obtain a classification means, which with a high rate of success may discern between the two attention classes examined here, i.e. speech and music.

b) Auto-Regressive Analysis (AR-Analysis)

Auto-Regressive analysis (AR-analysis) may be applied to obtain time-domain features from the signals measured by means of the electrodes. A feature obtained by AR-analysis will, as opposed to spectrum analysis, be dimensionless. This provides a big advantage in that changes in signal level, e.g. due to altered contact between electrodes and skin, will not affect the calculated feature. The AR-coefficients obtained by AR-analysis describe the temporal correlation structure in the signal.

The model for the AR-analysis assumes that the current sample, $s_n$, in a data sequence, $s_1, s_2, \ldots s_N$, can be predicted as a linearly weighted sum of the p most recent sample values, $s_{n-1}, s_{n-2}, \ldots s_{n-p}$. The model order is p and should be smaller than the data length, N. The predicted value of $s_n$, $\bar{s}$, may be written:

$$\bar{s} = -\sum_{i=1}^{p} a_{pi} s_{n-i}$$

where $a_{pi}$ is the weight of the AR model, the weight representing the coefficients of the model. In order to calculate these coefficients, the error between the actual value, $s_n$, and the predicted value, $\bar{s}_n$, should be considered. This error is called the forward prediction error, $e_{pn}$, and may be written:

$$e_{pn} = s_n - \bar{s}_n = s_n + \sum_{i=1}^{p} a_{pi} s_{n-i}$$

The power of the prediction error, E, denotes the mean of the squared prediction errors for all of the data sequence:

$$E = \frac{1}{N}\sum_{n=1}^{N} e_{pn}^2 = \frac{1}{N}\sum_{n=1}^{N}(s_n - \bar{s}_n)^2 = \frac{1}{N}\sum_{n=1}^{N}\left(s_n + \sum_{i=1}^{p} a_{pi} s_{n-1}\right)^2$$

Finally, the coefficients of the AR-model can be estimated by solving the following equation:

$$\frac{\partial E}{\partial a_{pi}} = 0, \text{ for } 1 \le i \le p$$

A fourth order AR-model was applied to obtain time domain features from the electrodes for the time period 4-24 seconds. Each signal was first segmented using sliding windows of length 100, and the data in each window was filtered from 0.01 Hz to 45 Hz using an EMD-based filtering technique. The coefficients of the AR-model in each window were determined and averaged over all trials.

Figure 11:
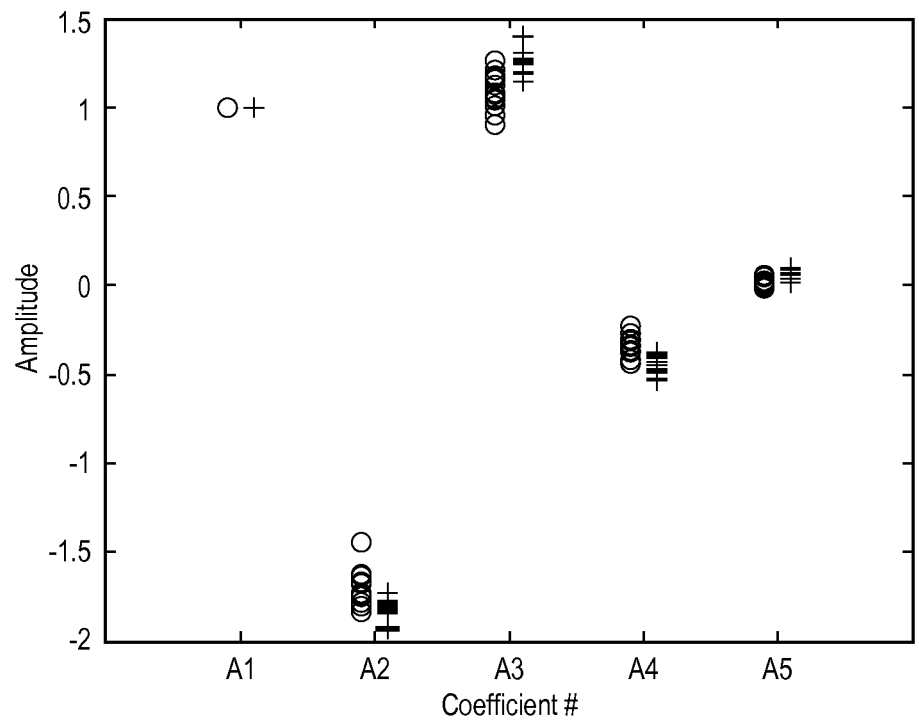

FIG. 11 illustrates the result, i.e. the coefficients of the AR-model, of AR-analysis performed on measurements obtained in an experiment of the type described above. Trials with attention to speech are denoted with "+", trials with attention to music with "o". The notable feature separation between speech and music trials illustrated in FIG. 11 reveals that it is possible to obtain a classification means, which with a high rate of success may discern between the two attention classes speech and music.

c) Asymmetry Analysis

By asymmetry analysis, the asymmetry ratio and mean frequency value can be combined to produce a 2D plot, which for a pair of channels indicates the level of asymmetry at each time and frequency. The mean asymmetry value for a specific frequency range is then determined and may be used for feature discrimination.

The asymmetry analysis is founded on an extension of the Empirical Mode Decomposition (EMD) known as Bivariate EMD (BEMD). Generally EMD is a data driven analysis method filtering or decomposing the signal in a number of components that may individually be ascribed an instantaneous frequency. By use of the extension to BEMD the two signals are decomposed in a number of components with conjugate identical or nearly identical frequency. One may from the amplitudes of such a pair of components calculate an asymmetry between the two signals at their average, instantaneous frequency.

To measure the asymmetry ratio in each frequency band for two EEG channels, $C_1$ and $C_2$, the complex signal $z=C_1+jC_2$ is first decomposed with BEMD. The complex intrinsic mode functions provide a set of common frequency components for the two channels $C_1$ and $C_2$. The Hilbert Huang transform is then applied to the real and imaginary components individually to obtain the corresponding instantaneous amplitudes $(a_1, a_2)$ and frequencies $(f_1, f_2)$. On this basis it may be shown, that the asymmetry ratio $(R_A)$ and the mean frequency $(f_{mean})$ can be obtained as:

$$R_A = \frac{|a_1 - a_2|}{a_1 + a_2},$$

$$f_{mean} = \frac{f_1 + f_2}{2}$$

Figure 12A:
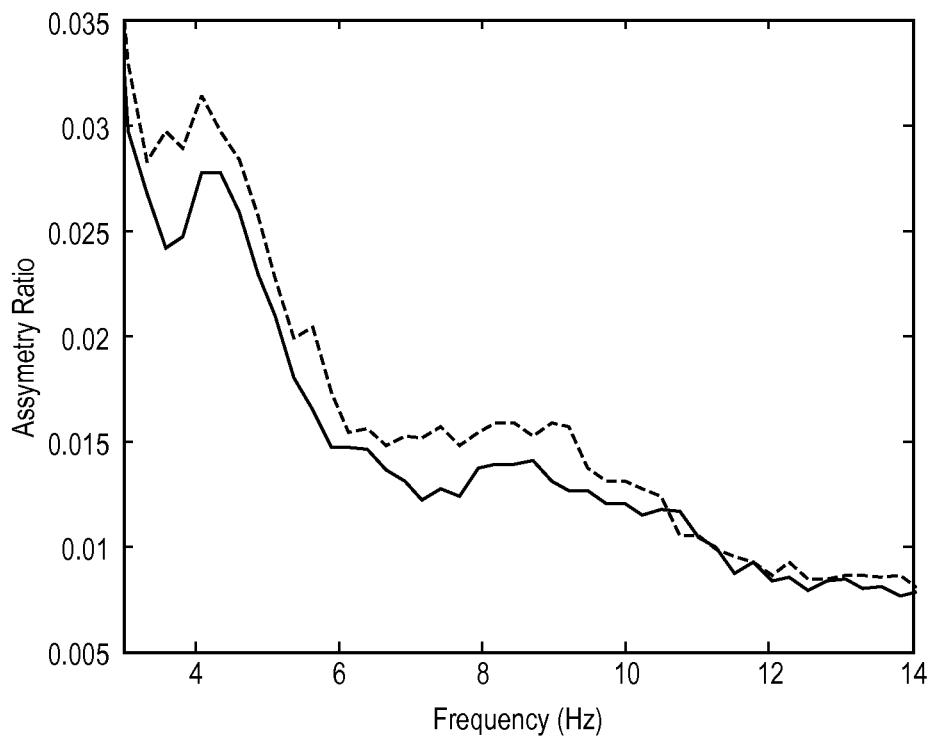
FIGS. 12a, 12b and 12c illustrate the results of an asymmetry analysis on a 20 trial measurement of brainwaves from a subject paying attention to speech and music, respectively, FIG. 12a showing the average asymmetry ration (AR) for all trials, FIG. 12b the AR for each trial and FIG. 12c the mean and variance of the values corresponding to each trial shown in FIG. 12b.
Figure 12B:
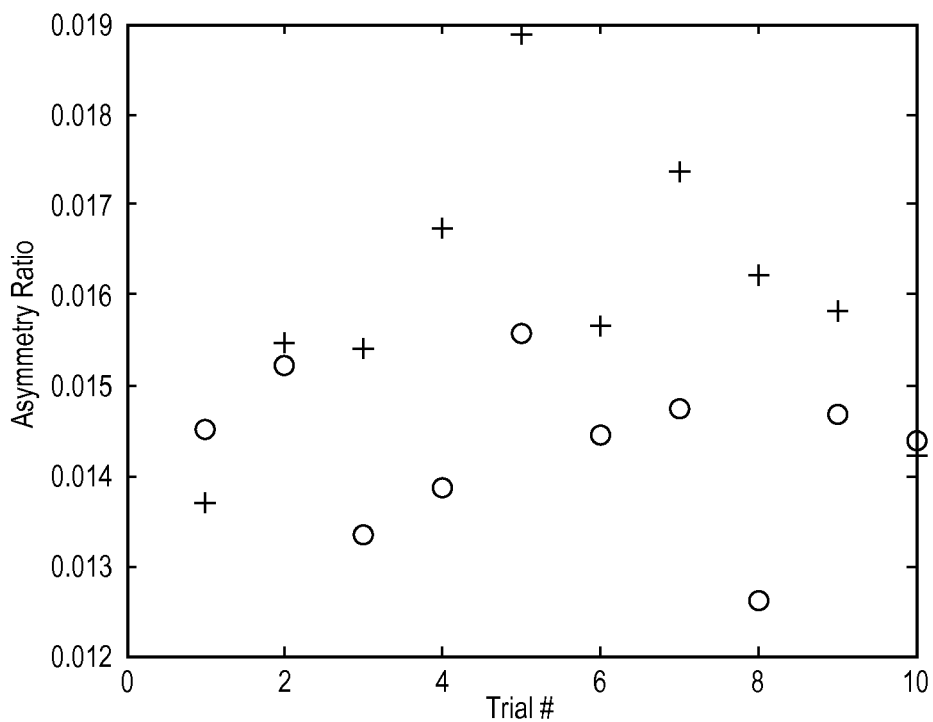
Figure 12C:
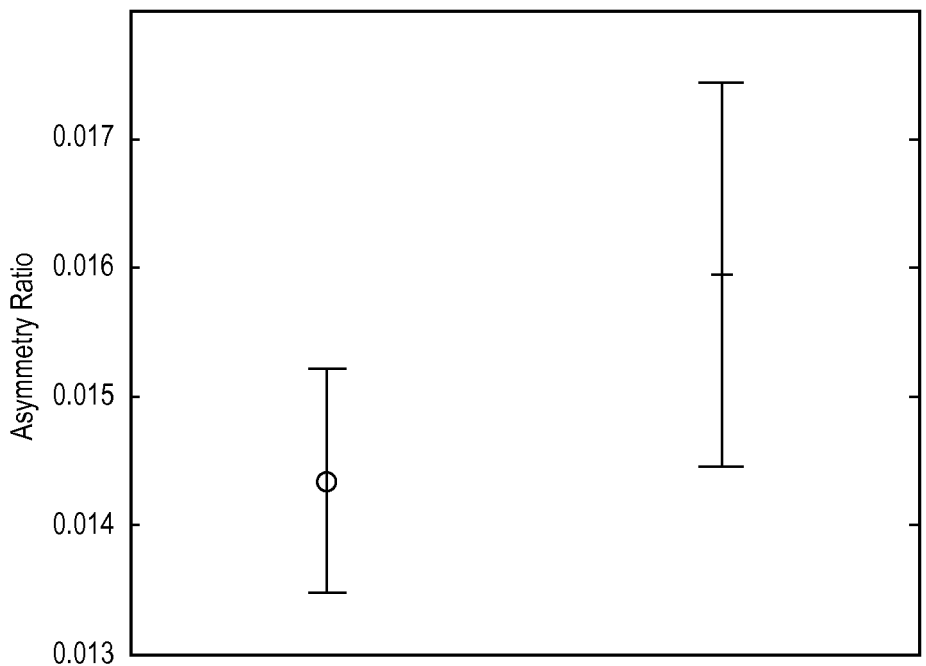

The results of such an asymmetry analysis is shown in FIGS. 12a, 12b and 12c for an experiment with 20 trials and otherwise as described above.

FIG. 12a shows the average asymmetry ratio over the frequency band 3-14 Hz. Trials with attention to speech are denoted with the dashed line, trials with attention to music with the solid line.

FIG. 12b shows the average asymmetry ratio for each individual trial in the frequency band 3-14 Hz. Trials with attention to speech are denoted with "+", trials with attention to music with "o".

Finally, FIG. 12c shows mean and variance for the values shown in FIG. 12b for the individual trials. The average for the trials with attention to speech is denoted with "+", the average for the trials with attention to music with "o".

The asymmetry analysis, particularly as illustrated in FIGS. 12b and 12c, showed that trials with attention to speech generally produce higher asymmetry ratios than trials with attention to music, thus contributing to the evidence in favour of the possibility of obtaining a classification means, which with a high rate of success may discern between the two attention classes speech and music. The asymmetry analysis furthermore showed that the optimal frequency band for feature separation varied between subjects.

d) Alpha Band Test with in-the-Ear Electrodes

A well documented characteristic of EEGs is that subjects exhibit a strong alpha band component (appearing at approximately 10 Hz) under eyes-closed conditions as opposed to under eyes-open conditions. This phenomenon can be used to evaluate the quality of an EEG recording.

Figure 13:
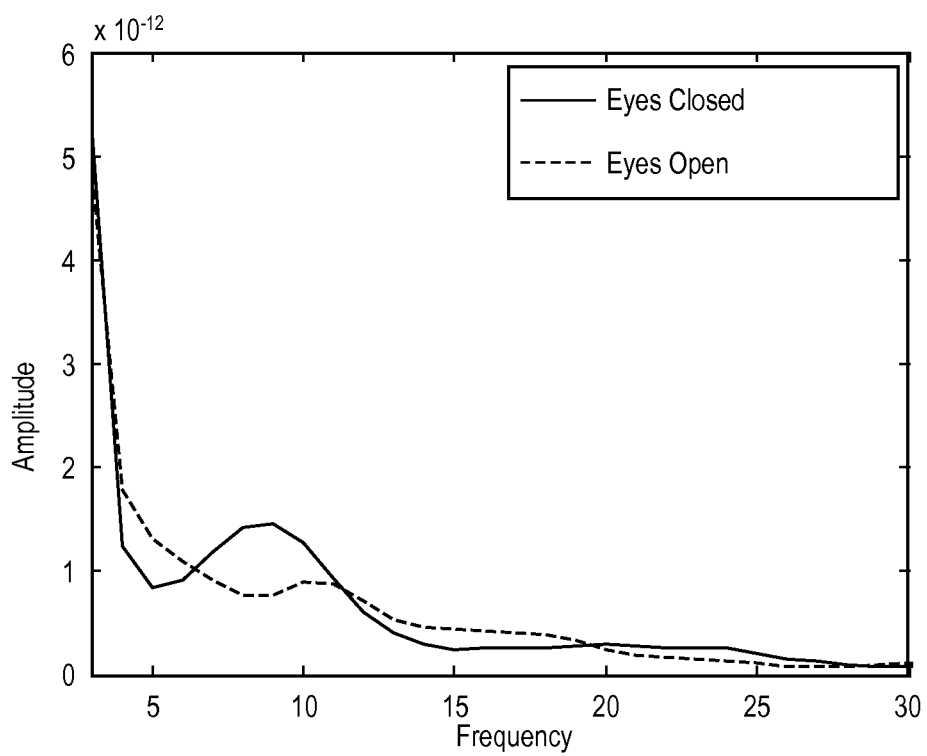
FIG. 13 illustrates the results of measurements conducted with an in-the-ear electrode corresponding to one of the electrodes shown in FIG. 2 with the subject having eyes open and closed, respectively, and with no further stimuli.

A subject was thus recorded under both eyes-closed and eyes-open conditions and with no further stimuli. The spectra for recordings obtained using an in-the-ear electrode corresponding to the electrode 204 in FIG. 2 are shown in FIG. 13. It can be seen that, as expected, the alpha band is larger under eyes-closed conditions. It can therefore be concluded, that the recordings obtained through the inner ear are consistent with documented EEG behaviour. These results render probable that the EEG-data measured by means of the in-the-ear electrode are valid EEG-data.

Finally, it should be noted that the above description of preferred embodiments is merely an example, and that the skilled person would know that numerous variations are possible without departing from the scope of the claims.

We claim:

1. A hearing aid comprising an amplifier, an input transducer, an output transducer and a signal processing device, said amplifier and said signal processing device being connected; at least two electrodes adapted for detecting electrical signals such as brain waves, the at least two electrodes being connected to a differential amplifier, which in turn is connected to the signal processing device; and means for modifying the operation of said hearing aid to obtain optimum intelligibility of the particular part of an acoustic image, without the user needing to consciously act to adapt the hearing aid, in response to the detected signals.

2. The hearing aid according to claim 1, wherein said signal processing device comprises feature extraction means for extracting at least one feature from a signal detected by means of said at least two electrodes and classifying means for classifying said at least one feature extracted by said feature extraction means.

3. The hearing aid according to claim 1, comprising a microphone connected to said feature extraction means.

4. The hearing aid according to claim 1, comprising means for comparing a signal detected by means of said at least two electrodes with a predefined set of attention classes.

5. The hearing aid according to claim 1, wherein said means for modifying the operation of the hearing aid modifies the operation of said hearing aid in response to said at least one feature extracted by said feature extraction means.

6. The hearing aid according to claim 1, wherein said means for modifying the operation of said hearing aid is activated by said hearing aid upon recognizing by means of said signal processing device a detected signal as comprising characteristics of at least one of a hearing threshold measurement, a hearing loss measurement, an attention focus measurement and a Brain-Computer Interface action measurement.

7. The hearing aid according to claim 1, wherein the at least two electrodes are arranged on or in a surface of a part of the hearing aid, preferably a plug of said hearing aid, such that when said hearing aid is worn by a user, said at least two electrodes are in physical contact with tissue of said user.

8. The hearing aid according to claim 1, comprising a fluid, conductive gel in connection with said at least two electrodes.

9. A method for adaptation of a hearing aid during use by a user, the method comprising the following steps:
providing at least one hearing aid according to claim 8,
measuring a brain signal from said user, and
adjusting the operation of said hearing aid in response to the detected signal to obtain optimum intelligibility of the particular part of an acoustic image, without the user needing to consciously act to adapt the hearing aid.

10. The method according to claim 9, comprising comparing said measured signal with a predefined set of attention classes.

11. The method according to claim 10 wherein said comparing step comprises:
extracting a feature from the measured brain signal by executing a first algorithm in said signal processing device, and
classifying said feature by executing a second algorithm in said signal processing device.

12. The method according to claim 10, wherein at least a part of said comparing step is performed using signal processing based on Empirical Mode Decomposition (EMD).

13. The method according to claim 9 comprising repeating said measuring, comparing and adjusting steps with a predetermined frequency.

14. The hearing aid according to claim 1, wherein said at least two electrodes are silver electrodes.

15. A hearing aid system comprising a first and a second hearing aid at least one of which is a hearing aid according to claim 1, each one of the first and the second hearing aid having an amplifier, at least one of the first and second hearing aid comprising a signal processing device comprising a feature extraction means and a classifying means, and wherein at least one of the first and second hearing aids comprises transmitting means for transmitting information to the second or first hearing aid, respectively.

16. The hearing aid system according to claim 15, wherein the signal processing means further comprises a class combining means.

17. The hearing aid system according to claim 15 wherein at least one of said feature extraction means, said classification means and said class combining means of said first and second hearing aid, respectively, are interconnected by means of said transmitting means.

18. The hearing aid system according to claim 15, wherein said transmitting means is wireless.

19. A hearing aid comprising an amplifier, an input transducer, an output transducer and a signal processing device, said amplifier and said signal processing device being connected; at least two electrodes adapted for detecting electrical signals such as brain waves, the at least two electrodes being connected to a differential amplifier, which in turn is connected to the signal processing device; and means for modifying the operation of said hearing aid in response to the detected signals.

20. A hearing aid comprising an amplifier, an input transducer, an output transducer and a signal processing device, said amplifier and said signal processing device being connected; at least two electrodes adapted for detecting electrical signals, the at least two electrodes being connected to a differential amplifier, which in turn is connected to the signal processing device; and means for modifying the operation of said hearing aid in response to the detected signals, wherein said means for modifying the operation of said hearing aid is activated by said hearing aid upon recognizing by means of said signal processing device a detected signal as comprising characteristics of at least one of a hearing threshold measurement, a hearing loss measurement, an attention focus measurement and a Brain-Computer Interface action measurement.

* * * * *